United States Patent
Haber et al.

[11] Patent Number: 6,160,180
[45] Date of Patent: Dec. 12, 2000

[54] TERTIARY PHOSPHANES CONTAINING ALKYLENE GLYCOL GROUPS

[75] Inventors: Steffen Haber, Königstein; Hans-Jerg Kleiner, Kronberg; Sandra Bogdanovic, Frankfurt; Helmut Bahrmann, Hamminkeln; Carl-Dieter Frohning, Wesel, all of Germany

[73] Assignee: Celanese Chemicals Europe GmbH, Frankfurt am Main, Germany

[21] Appl. No.: 09/230,538
[22] PCT Filed: Jul. 21, 1997
[86] PCT No.: PCT/EP97/03927
§ 371 Date: Apr. 22, 1999
§ 102(e) Date: Apr. 22, 1999
[87] PCT Pub. No.: WO98/04568
PCT Pub. Date: Feb. 5, 1998

[30] Foreign Application Priority Data

Jul. 29, 1996 [DE] Germany .......................... 196 30 534
Apr. 30, 1997 [DE] Germany .......................... 197 18 196

[51] Int. Cl.[7] ................. C07F 9/50; C07F 9/28; C08F 30/02
[52] U.S. Cl. ................. 568/12; 568/13; 568/15; 568/17; 526/274; 526/275
[58] Field of Search ................. 568/8, 12, 13, 568/15, 17; 526/275, 276, 274

[56] References Cited

U.S. PATENT DOCUMENTS

4,556,740  12/1985  Hansen ........................................ 568/13

OTHER PUBLICATIONS

CA:126:199246 abs of Mol Catal A :Chem by Jin 116 (1–2) pp. 55–58, 1997.
CA:130:95347 abs of J Organomet Chem by Chen 571 (2) pp. 201–204, 1998.
CA:123:286929 abs of Macromolecules by Choi 28(24) pp. 8419–8421, 1995.
J. Chem. Soc., Perkins Trans. 1, 1996, Tertfort et al., pp. 1467–1479.
Chemical Abstracts, vol. 125, No. 3, Jul. 15, 1996, p. 855.
J. Org. Chem., vol. 45, 1980, pp. 1156–1158.
Chemical Abstracts, vol. 105, No. 7, Aug. 18, 1986, p. 622.

*Primary Examiner*—Jean F Vollano
*Attorney, Agent, or Firm*—Frommer Lawrence & Haug

[57] ABSTRACT

A compound is disclosed having the formula (I), in which m equals 1 to 1000; x equals 0 to 4; W is a group of formulas $-CH_2-CH_2-$, $-CH(CH_3)CH_2-$ or $-CH_2CH(CH_3)-$; R is hydrogen, a straight-chain or branched-chain $C_1-C_5$ alkyl radical; or a group of formulas (a) or (b), in which a, b, c, d and e independently represent a number from 0 to 1000, at least one of the numbers represented by a, b, c, d and e being higher than 0; $R^5$, $R^6$, $R^7$, $R^8$ and $R^9$ are the same or different and represent hydrogen, $C_1-C_5$ alkyl or a group of formula (c); $R^1$ and $R^2$ are the same or different and represent a straight-chain, a branched-chain or a cyclic $C_1-C_{30}$ alkyl radical or $C_6-C_{10}$ aryl radical which is non-substituted or substituted by one to five $C_1-C_3$ alkyl radicals, or $R^1$ and $R^2$ form together with the trivalent P atom form a dibenzophospholyl of formula (d) or a 3,4-dimethylpholyl of formula (e); and L stands for $C_1-C_5$ alkyl, $C_1-C_5$ alkoxy, $NO_2$, $NR^3R^4$, $R^3$ and $R^4$ independently representing hydrogen or $C_1-C_4$ alkyl, or for Cl or OH.

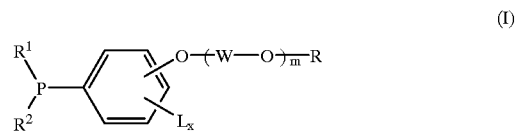

(I)

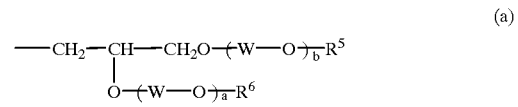

(a)

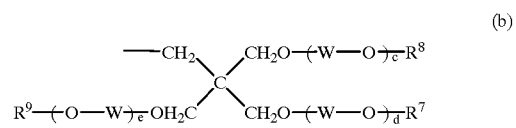

(b)

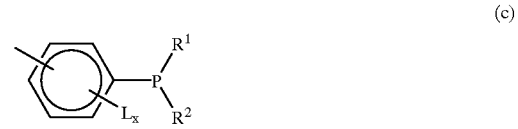

(c)

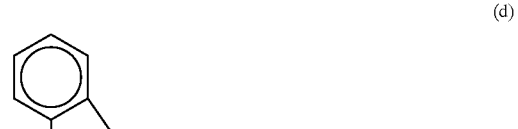

(d)

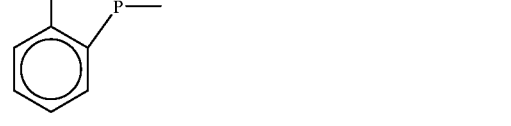

(e)

11 Claims, No Drawings

TERTIARY PHOSPHANES CONTAINING ALKYLENE GLYCOL GROUPS

This application is the national phase of PCT/EP97/03927, filed Jul. 21, 1997, now WO98/04568.

The present invention is in the field of organic phosphorus chemistry.

The invention relates to novel tertiary phosphines carrying alkylene glycol groups and to their preparation by nucleophilic substitution.

Complex compounds which contain, as central atom, a metal from subgroup 8 of the Periodic Table of the Elements and, as ligands, P(III) compounds, e.g. phosphines or phosphites, and optionally further groups able to form complexes, have been used increasingly in recent years as catalysts for syntheses in organic chemistry. For example, the reaction of olefins with synthesis gas to give aldehydes (hydroformylation), which is carried out industrially on a large scale, is carried out in the presence of catalyst systems consisting of cobalt and, in particular, rhodium and triphenylphosphine. Also, for the reaction of methanol with synthesis gas to give higher alcohols (homologization), catalysts based on complex compounds containing phosphine have proven successful. In most of the above cases, the ligands are present in excess, so that the catalyst system consists of complex compound and free ligand. Depending on the solubility of the catalysts in organic media, the reactions take place in homogeneous phase.

Instead of in homogeneous phase, it is also possible to carry out the reaction in heterogeneous, multiphase reaction systems. An advantage of this process variant is the simple and gentle separation of the catalyst dissolved in water from the water-insoluble reaction product. This principle is used, for example, in the process described in DE-C2-27 00 904 for the preparation of nitriles by the addition reaction of hydrogen cyanide to unsaturated organic compounds containing at least one ethylenic double bond. In the preparation of aldehydes by reaction of olefins with carbon monoxide and hydrogen according to the process described in DE-C2-26 27 354, rhodium in metallic form or in the form of its compounds together with a water-soluble phosphine, e.g. the alkali metal salt of tri(m-sulfonatophenyl)phosphine ("TPPTS") is used as catalyst. Other examples of reactions with a heterogeneous catalyst phase can be found in Agnew. Chem. 1993, 105, 1588 ff.

J. Chem. Soc., Perkin Trans. 1 1996, 1467, discloses chiral phosphine ligands which are used for the asymmetric Grignard cross-coupling. Chem. Abstracts, Vol. 125, no. 33125x, describes phosphine compounds which contain three polyether radicals per phosphorus atom. J. Organ. Chem. 1980, 1156 and Chem. Abstracts. Vol. 105, no. 60677x refer to biphosphine compounds bridged via a polyether chain.

Two-phase processes have also proven highly successful on an industrial scale. Recent work has further improved the processes. For example, attempts are being made to increase the activity of the catalysts by modifying the complex ligands and to extend their effectiveness in order to further reduce the specific catalyst requirement, both metal and ligand, and thus the product costs. Economic reasons are also a decisive factor in working toward a significant reduction in the phosphine/metal ratio. Finally, there are efforts to solve the product-specific problems associated with known processes. Moreover, the search is on for novel fields of application for these versatile catalyst systems.

The object of the present invention was to provide novel phosphines which are suitable, in particular, for use in catalyst systems for organic syntheses.

The present invention provides tertiary phosphines of the formula (I)

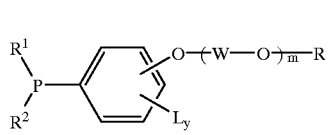

in which m is a number from 2 to 300, preferably from 2 to 100;

y is a number from 0 to 4, preferably 0 or 1;

a, b, c, d and e independently of one another are numbers from 0 to 1000, at least one of the numbers a, b, c, d and e being greater than 0;

$R^5$, $R^6$, $R^7$, $R^8$, and $R^9$ are identical or different and are hydrogen, $C_1$–$C_5$-alkyl or a group of the formula

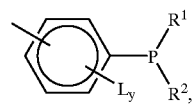

$R^1$ and $R^2$ are identical or different and are a straight-chain, branched or cyclic $C_1$–$C_{30}$-alkyl radical or $C_6$–$C_{10}$-aryl radical, which is unsubstituted or substituted by from one to five $C_1$–$C_3$-alkyl radicals, or $R^1$ and $R^2$, together with the trivalent P atom, form a dibenzophospholyl of the formula

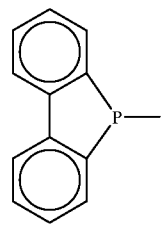

or a 3,4-dimethylphospholyl of the formula

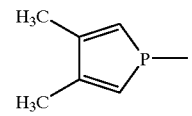

L is $C_1$–$C_5$-alkyl, $C_1$–$C_5$-alkoxy, $NO_2$, $NR^3R^4$, where $R^3$ and $R^4$ independently of one another are hydrogen or $C_1$–$C_4$-alkyl, or L is Cl or OH and x is a number from 0 to 4, preferably 0 or 1.

The alkylene glycol groups on the phenyl ring can be in the ortho, meta or para position relative to the phosphorus atom. The oxalkylene chain on which the group —(W—O—)$_m$ is based can consist exclusively of ethylene oxide units or exclusively of propylene oxide units or of a combination of these units in any desired order.

Of particular interest are compounds of the formula (I) in which $R^1$ and $R^2$ are identical and are each a straight-chain or branched $C_1$–$C_6$-alkyl radical, a cyclohexyl radical or a phenyl radical.

Also of particular interest are compounds of the formula (I) in which R is hydrogen, methyl, ethyl, n-propyl, n-butyl or a group of the formula

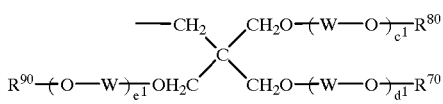

in which $c^1$, $d^1$ and $e^1$ independently of one another are a number from 1 to 500, in particular from 2 to 300, and $R^{70}$, $R^{80}$ and $R^{90}$ are identical or different and are hydrogen, methyl, ethyl, n-propyl or n-butyl.

Also of particular interest are compounds of the formula (I) in which L is methoxy, ethoxy, methyl, ethyl or OH, or in which x is 0.

Examples of compounds of the formula (I) are methyl triphenylphosphin-4-yl triethylene glycol ether,
methyl triphenylphosphin-3-yl triethylene glycol ether,
methyl triphenylphosphin-2-yl triethylene glycol ether, and compounds containing relatively long oxalkyl chains, the ethoxy and propoxy units being in any desired order and usually forming a product mixture:

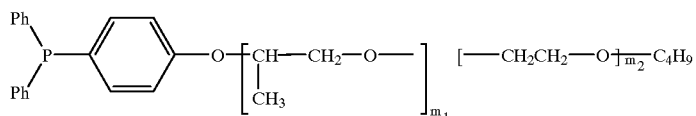

in which $m_1$ and $m_2$ are each about the number 16 and Ph is phenyl;

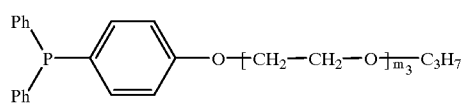

in which $m_3$ is a number of about 22;

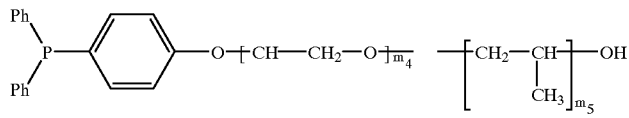

in which $m_4$ is about 84 and $m_5$ is about 21,

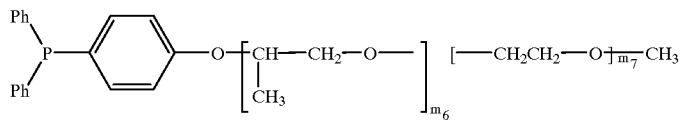

in which $m_6$ is about 22 and $m_7$ is 5.5,

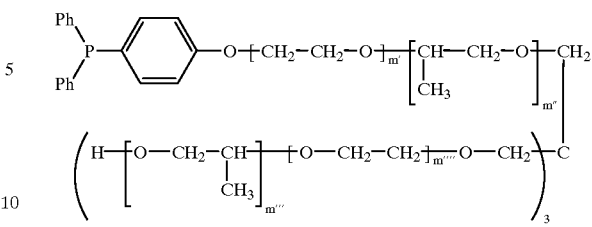

in which m' is about 10, m" is from about 2 to 3, m'" is from about 7 to 8 and m"" is about 30.

The distribution of the oxalkylene groups in the product, in particular the ratio and the arrangement (order) of oxethylene to ox-2-propylene groups is determined by the starting materials used. The latter are prepared by the addition reaction of ethylene oxide and propylene oxide to water or alcohols. The addition and arrangement takes place randomly. The starting materials used are commercial products from Hoechst AG.

The invention also provides a process for the preparation of a compound of the formula (I) which comprises deprotonating a hydroxyphenylphosphine of the formula (II)

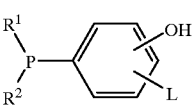

(II)

using a base to give the corresponding phenoxide, and reacting it with a compound of the formula (III)

X—(—W—O—)$_m$—R  (III)

in which W, R and m are as defined above and X is a nucleophilically substitutable leaving group, to give the compound of the formula (I).

Examples of the nucleophilically substitutable leaving group X are ortho-, meta- or para-toluenesulfonate, methanesulfonate, trifluoroacetate, trifluoromethanesulfonate, nonafluorobutylsulfonate, benzenesulfonate, p-nitrobenzenesulfonate, Cl, Br or I.

Suitable bases are, for example, NaOH, KOH, NaH, KH or trialkylamines. Preference is given to NaH, KH, triethylamine and KOH.

The reaction is expediently carried out at temperatures between 20 and 100° C., preferably between 60 and 90° C. Since the deprotonation step is usually exothermic, at this point in the synthesis, cooling may be expedient, for example to from 0 to 20° C.

The process according to the invention can be carried out in the presence or absence of organic solvents. Suitable organic solvents are, in particular, dimethylformamide, toluene or ethyl acetate. It is further advantageous to carry out the reaction according to the invention under an inert-gas atmosphere.

The compounds of the formula (II) can be prepared by methods known from the literature, for example in accordance with O. Neunhoeffer et al., Chem. Ber. 94 (1961), 2514.

The compounds of the formula (I) are suitable as ligands in metal-complex-catalyzed organic reactions or as stabilizers for polyalkylene glycols.

In the examples below, "TLC" means thin-layer chromatogram, "GC" means gas chromatogram, "EE" means ethyl acetate and "DMF" means dimethylformamide.

EXAMPLE 1

Triphenylphosphin-4-yl Triethylene Glycol Methyl Ether

| Materials: | | |
|---|---|---|
| 200 g (0.7195 mol) | p-hydroxytriphenylphosphine | 278 g/mol |
| 18 g (0.75 mol) | sodium hydride | 24 g/mol |
| 265 g (0.75 mol) | p-tosyl triethylene glycol methyl ether | (90% strength) |

Procedure Protective-gas technique 200 g of p-hydroxytriphenylphosphine are dissolved in 1 liter of DMF. Sodium hydride is added slowly in portions (exothermic), as a result of which hydrogen begins to evolve. The mixture is stirred for 1 hour at room temperature. 265 g of p-tosyl triethylene glycol methyl ether (90% strength) are added to the mixture, which is then stirred for 1 hour at 80° C. The reaction is monitored from the TLC (eluent: EE/n-heptane=1/1).
Work-up The solvent is removed under a high vacuum, and 1 liter of water and 2 liters of tert-butyl methyl ether are added to the residue. The organic phase is separated off. The aqueous phase is extracted by shaking with 2×500 ml of tert-butyl methyl ether. The combined organic phases are dried over Na$_2$SO$_4$, filtered and reduced by evaporation.
TLC check: Eluent:

EE/n-heptane 1/1
Product: R$_f$=0.7
Tosyl ether: R$_f$=0.4

The crude product is applied to 1.2 times the amount by weight of silica gel and chromatographed over a column.

Column chromatography: 2 kg of silica gel, eluent EE/n-heptane 1/1
Yield: ~70% of theory of colorless, very viscous oil
$^{31}$P-NMR (CD$_2$Cl$_2$): −5.0 ppm

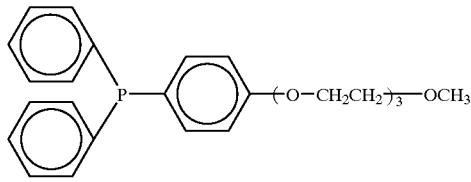

EXAMPLE 2

Triphenylphosphin-3-yl Triethylene Glycol Methyl Ether

| Materials: | | |
|---|---|---|
| 200 g (0.7195 mol) | m-hydroxytriphenylphosphine | 278 g/mol |
| 18 g (0.75 mol) | sodium hydride | 24 g/mol |
| 265 g (0.75 mol) | p-tosyl triethylene glycol methyl ether | (90% strength) |

Procedure: Protective-gas technique 200 g of m-hydroxytriphenylphosphine are dissolved in 1 liter of DMF. Sodium hydride is added slowly in portions (exothermic), as a result of which hydrogen begins to evolve. The mixture is stirred for 1 hour at room temperature. 265 g of p-tosyl triethylene glycol methyl ether (90% strength) are added to the mixture, which is then stirred for 1 hour at 80° C. The reaction is monitored from the TLC (eluent: EE/n-heptane=1/1).
Work-up The solvent is removed under a high vacuum, and 1 liter of water and 2 liters of tert-butyl methyl ether are added to the residue. The organic phase is separated off. The aqueous phase is extracted by shaking with 2×500 ml of tert-butyl methyl ether. The combined organic phases are dried over Na$_2$SO$_4$, filtered and reduced by evaporation.
TLC check:

Eluent: EE/n-heptane 1/1
Product: R$_f$=0.7
Tosyl ether: R$_f$=0.4

The crude product is applied to 1.2 times the amount by weight of silica gel and chromatographed over a column.

Column chromatography: 2 kg of silica gel, eluent EE/n-heptane 1/1
Yield: ~70% of theory of colorless, very viscous oil
$^{31}$P-NMR (CD$_2$Cl$_2$): −5.1 ppm

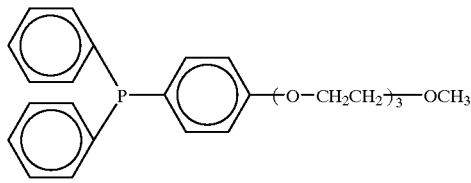

EXAMPLE 3

(Triphenylphosphin-2-yl) Triethylene Glycol Methyl Ether

| Materials: | | |
|---|---|---|
| 200 g (0.7195 mol) | o-hydroxytriphenylphosphine | 278 g/mol |
| 18 g (0.75 mol) | sodium hydride | 24 g/mol |
| 265 g (0.75 mol) | p-tosyl triethylene glycol methyl ether | (90% strength) |

Procedure: Protective-gas technique 200 g of o-hydroxytriphenylphosphine are dissolved in 1 liter of DMF. Sodium hydride is added slowly in portions (exothermic), as a result of which hydrogen begins to evolve. The mixture is stirred for 1 hour at room temperature. 265 g of p-tosyl triethylene glycol methyl ether (90% strength) are added to the mixture, which is then stirred for 1 hour at 80° C. The reaction is monitored from the TLC (eluent: EE/n-heptane=1/1).

Work-up

The solvent is removed under a high vacuum, and 1 liter of water and 2 liters of tert-butyl methyl ether are added to the residue. The organic phase is separated off. The aqueous phase is extracted by shaking with 2×500 ml of tert-butyl methyl ether. The combined organic phases are dried over $Na_2SO_4$, filtered and reduced by evaporation.

TLC check:
Eluent: EE/n-heptane 1/1
Product: $R_f$=0.7
Tosyl ether: $R_f$=0.4

The crude product is applied to 1.2 times the amount by weight of silica gel and chromatographed over a column.

Column chromatography: 2 kg of silica gel, eluent EE/n-heptane 1/1

Yield: ~70% of theory of colorless, very viscous oil
$^{31}$P-NMR ($CD_2Cl_2$): –23 ppm

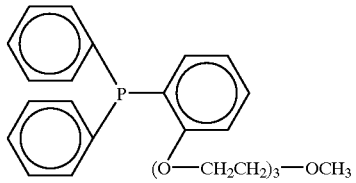

Preparation of p-toluenesulfonyl Triethylene Glycol Methyl Ether 200 g of p-toluenesulfonyl chloride and 172.4 g of triethylene glycol monomethyl ether are dissolved in 1 liter of dichloromethane and cooled to 0° C. With vigorous stirring, 236.3 g of freshly powdered potassium hydroxide are metered in at a rate such that the temperature does not exceed 5° C. The mixture is maintained at 0° C. for 3 hours. 1 liter of dichloromethane and 1.2 liters of iced water are added. If more solids form, a further 0.5 liter of iced water are added. The organic phase is separated off and washed with 0.3 liter of saturated sodium chloride solution. It is dried over $Na_2SO_4$ and evaporated to dryness under reduced pressure.

Yield: 313.4 g; GC: 92.6% strength

EXAMPLE 4

Preparation of p-(P41/300)-triphenylphosphine

P41/300 is taken to mean a pentaerythritol etherified with ethylene oxide and propylene oxide in a molar ratio of 4:1, the product having a viscosity of 300 mPa.s and about 84 ethoxy and about 21 propoxy groups.

28.33 g (101.8 mmol) of p-hydroxytriphenylphosphine are dissolved in 40 ml of DMF. 101.8 mmol of potassium hydroxide are added, and the mixture is heated at 80° C. for 1 hour. 509 g (102 mmol) of P41/300-tosylate are then added, and the mixture is stirred for 2 hours at 80° C., the DMF then being evaporated off under reduced pressure. The product is completely soluble in water at 50° C. It emulsifies in water at temperatures <20° C. and >80° C. The process is reversible.

$^{31}$P-NMR ($CD_2Cl_2$): –5.2 ppm

EXAMPLE 5

Preparation of m-(P41/300)-triphenylphosphine 28.33 g of m-hydroxytriphenylphosphine are dissolved in 40 ml of DMF. 101.8 mmol of potassium hydroxide are added, and the mixture is heated at 80° C. for 1 hour. 509 g (102 mmol) of P41/300-TOS are then added, and the mixture is stirred for 2 hours at 80° C. The product is completely soluble in water at 50° C. It emulsifies in water at temperatures <20° C. and >80° C. The process is reversible.

$^{31}$P-NMR ($CD_2Cl_2$): –5.1 ppm

EXAMPLE 6

Preparation of o-(P41/300)-triphenylphosphine 28.33 g of o-hydroxytriphenylphosphine are dissolved in 40 ml of DMF. 101.8 mmol of potassium hydroxide are added, and the mixture is heated at 80° C. for 1 hour. 509 g (102 mmol) of P41/300-TOS are then added, and the mixture is stirred for 2 hours at 80° C. The product is completely soluble in water at 50° C. It emulsifies in water at temperatures <20° C. and >80° C. The process is reversible.

$^{31}$P-NMR ($CD_2Cl_2$): –23.5 ppm

Preparation of P41/300-tosylate 500 g of P41/300 and 19.07 g of p-toluenesulfonyl chloride are dissolved in 1 liter of dichloromethane. 15.18 g of triethylamine are then added. The mixture is heated under reflux for 2 hours. 250 ml of water are added to the reaction mixture, the aqueous phase is separated from the organic phase, and the organic phase is dried with $Na_2SO_4$.

Yield: 509.7 g

EXAMPLES 7 TO 16

General Preparation Procedure for the Feed Materials Used in Examples 7 to 16

The polyalkylene glycols used in the general procedure are discussed in more detail below.

PEG 200 is taken to mean a mixture of polyethylene glycols of the formula $H(OCH_2CH_2)_mOH$ in which m is an integer from 3 to 6, PEG 400 is taken to mean a mixture of polyethylene glycols of the formula $H(OCH_2CH_2)_mOH$ in which m is an integer from 7 to 10, PEG 600 is taken to mean a mixture of polyethylene glycols of the formula $H(OCH_2CH_2)_mOH$ in which m is an integer from 11 to 16, PEG 1000 is taken to mean a mixture of polyethylene glycols of the formula $H(OCH_2CH_2)_mOH$ in which m is an integer from 15 to 30, and PEG 1500 is taken to mean a mixture of polyethylene glycols of the formula $H(OCH_2CH_2)_mOH$ in which m is an integer from 25 to 35. Each of these mixtures is assigned a corresponding mean molecular weight of 200 (PEG 200), about 400 (PEG 400), about CH₂CH(CH₃) being 4:1. This mixture is assigned a corresponding mean molecular weight of 1000.

P41/300 is taken to mean a mixture of compounds of the formula C{(OW)$_m$OH}$_4$, where m is an integer between 90 and 120 and W is a group of the formulae —CH₂CH₂—, —CH(CH₃)CH₂— or —CH₂CH(CH₃)—, the ratio of ethylene groups (—CH₂CH₂—) and methylethylene groups (CH₂CH(CH₃) being 4:1. This mixture is assigned a corresponding mean molecular weight of 5000.

B11/50 is taken to mean a mixture of compounds of the formula n-C₄H₉—(OW)$_m$OH, where m is an integer between 11 and 21 and W is a group of the formulae —CH₂CH₂—, —CH(CH₃)CH₂— or —CH₂CH(CH₃)—, the ratio of ethylene groups (—CH₂CH₂—) and methylethylene groups (—CH(CH₃)CH₂— or —CH₂CH(CH₃)—) being 1:1. This mixture is assigned a corresponding mean molecular weight of 1700.

In the formulae, m is in each case an average value, meaning that the formula given has the mean molecular weight of the particular substance class.

1. O-Methyl-polyalkylene glycol ether

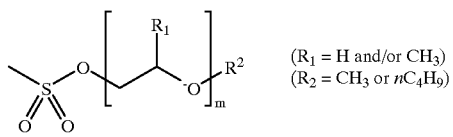

($R_1$ = H and/or CH₃)
($R_2$ = CH₃ or $nC_4H_9$)

General procedure: 4.7 g (60 mmol) of methanesulfonyl chloride are added to 50 mmol of polyalkylene glycol dissolved in 500 ml of dichloromethane; 10.4 ml (75 mmol) of triethylamine are then added dropwise at room temperature with stirring. Polyalkylene glycol may be taken to mean the compounds discussed above. The reaction solution is left to stand for about 16 hours at room temperature [in the case of (e) for 8.5 hours under reflux].

(a) O-Mesyl-[M 350]

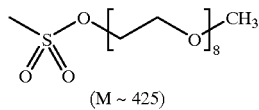

(M ~ 425)

Feed: 0.2 mol of M 350, (molecular weight ~350)
Yield: 83 g (97.5%), viscous oil
TLC, $R_f$=0.6 (CH₂Cl₂:C₂H₅OH=9:1)
¹H-NMR: (CDCl₃) δ [ppm] 3.08 (OSO₂CH₃, s 3H), 3.38 (OCH₃, s 3H), 3.52–4.40 (OCH₂, m about 32)
Free OH function no longer present (acetic anhydride/pyridine method)

(b) O-Mesyl-[M 500]

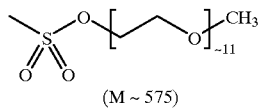

(M ~ 575)

Feed: 0.2 mol of M 500, (molecular weight ~500)
Yield: 111.6 g (97%), viscous oil
TLC, $R_f$=0.5 (CH₂Cl₂:C₂H₅OH=9:1)
¹H-NMR: (CDCl₃) δ [ppm] 3.08 (OSO₂CH₃, s 3H), 3.38 (OCH₃, s 3H), 3.52–4.40 (OCH₂, m about 45H)
Free OH function no longer present (acetic anhydride/pyridine method)

(c) O-Mesyl-[M 750]

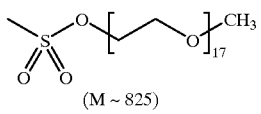

(M ~ 825)

Feed: 0.1 mol of M 750, (molecular weight ~750)
Yield: 82.8 g (97.5%), viscous oil
TLC, $R_f$=0.59 (CH₂Cl₂:C₂H₅OH=9:2)
¹H-NMR: (CDCl₃) δ [ppm] 3.08 (OSO₂CH₃, s 3H), 3.38 (OCH₃, s 3H), 3.52–4.40 (OCH₃, m about 68H)
Free OH function no longer present (acetic anhydride/pyridine method)

(d) O-Mesyl-[M 41/40]

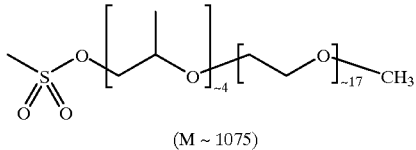

(M ~ 1075)

Feed: 0.1 mol of M 41/40, (molecular weight ~1000)
Yield: 99.6 g (92.6%), viscous oil
¹H-NMR: (CDCl₃) δ [ppm] 3.08 (OSO₂CH₃, s 3H), 3.38 (OCH₃, s 3H), 1.15 and 1.38 (CCH₃, 2d 12H), 3.35–4.40 (OCH₂ and OCH, m about 80H)
Free OH function no longer present (acetic anhydride/pyridine method)

(e) O-Mesyl-[B 11/50]

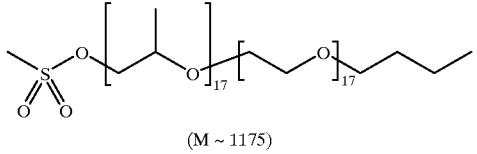

(M ~ 1175)

Feed: 0.1 mol of B 11/50, (molecular weight ~1700)
Yield: 173 g (97%), viscous oil
¹H-NMR: (CDCl₃) δ [ppm] 0.92 (Bu CH₃, t 3H), 1.15 and 1.38 (CCH₃, CCH₂CH₂C, m 55H), 3.08 (OSO₂CH₃, "s" 3H), 3.35–4.40 (OCH₂ and OCH, m about 121H)
Free OH function no longer present (acetic anhydride/pyridine method)

2. O-Mesyl-polyethylene glycols

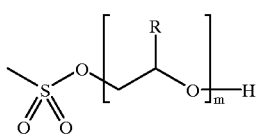

[(R=H and/or CH₃)]

General procedure: 11.46 g (100 mmol) of methanesulfonyl chloride are added to 100 mmol of polyethylene glycol dissolved in 1000 ml of dichloromethane; 12.2 g (120 mmol) of triethylamine are then added dropwise at 0° C. with stirring. The reaction solution is then left to stand at room temperature for about 16 hours. For work-up, the reaction solution is washed with 3×200 ml of 5% strength aqueous citric acid, with 2×200 ml of saturated sodium hydrogencarbonate solution and once with 200 ml of water. The dichloromethane phase is then dried with magnesium sulfate, and the solvent is evaporated off. The reaction produced consists of a mixture of starting polyalkylene glycol, mono- and dimesylated polyalkylene glycol; the desired monomesylated product can be separated off by column chromatography (silica gel). (See Examples).

To ensure the structures of the target compounds and the purities, the proton ratios in the $^1$H NMR spectra and the quantitative determination of the OH concentration by the acetic anhydride/pyridine method (titration of the amount of acetic acid liberated), thin-layer chromatographic and HPLC methods were used.

The abbreviation $R_f$ is the retention quotient in thin-layer chromatography (TLC).

(a) O-Mesyl-[PEG 200]

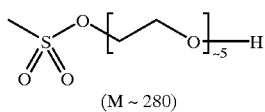

(M ~ 280)

Feed: 0.5 mol of PEG 200, (molecular weight ~200)
Purification: column chromatography [silica gel ($\phi$=10 cm, h=100 cm)]CH$_2$Cl$_2$ then CH$_2$Cl$_2$:C$_2$H$_5$OH=18:2
Yield: 24 g (17.3%), viscous oil
TLC, $R_F$=0.37 (CH$_2$Cl$_2$:C$_2$H$_5$OH=9:1)
$^1$H-NMR: (CDCl$_3$) d [ppm] 2.70 (OH, s 1H), 3.08 (OSO$_2$CH$_3$, "s" 3H), 3.58–4.40 (OCH$_2$, m about 18H)
One OH function/molecule still present (acetic anhydride/pyridine method)

(b) O-Mesyl-[PEG 600]

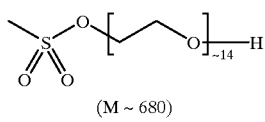

(M ~ 680)

Feed: 0.17 mol of PEG 600, (molecular weight ~600)
Purification: column chromatography [silica gel ($\phi$=10 cm, h=100 cm)]CH$_2$Cl$_2$ then CH$_2$Cl$_2$:C$_2$H$_5$OH=18:2
Yield: 29.5 g (26%), viscous oil
TLC, $R_F$=0.36 (CH$_2$Cl$_2$:C$_2$H$_5$OH=9:1)
$^1$H-NMR: (CDCl$_3$) δ [ppm] 2.73 (OH, s 1H), 3.08 (OSO$_2$CH$_3$; s 3H), 3.59–4.40 (OCH$_2$, m about 55H)
One OH function/molecule still present (acetic anhydride/pyridine method)

(c) O-Mesyl-[PEG 1000]

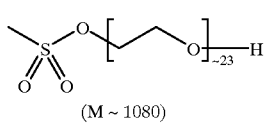

(M ~ 1080)

Feed: 0.1 mol of PEG 1000, (molecular weight ~1000)
Purification: column chromatography [silica gel ($\phi$=10 cm, h=100 cm)]acetone
Yield: 32.2 g (30%), waxy product
TLC, $R_F$=0.34 (CH$_2$Cl$_2$:C$_2$H$_5$OH=5:1)
$^1$H-NMR: (CDCl$_3$) δ [ppm] 2.65 (OH, s 1H), 3.08 (OSO$_2$CH$_3$; s 3H), 3.57–4.40 (OCH$_2$, m about 92H)
One OH function/molecule still present (acetic anhydride/pyridine method)

(d) O-Mesyl-[PEG 1500]

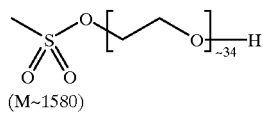

(M~1580)

Feed: 0.1 mol of PEG 1500, (molecular weight ~1500)
Purification: column chromatography [silica gel ($\phi$=10 cm, h=100 cm)] acetone
Yield: 20 g (19%)
TLC, $R_F$=0.45 (CH$_2$Cl$_2$:C$_2$H$_5$OH=4:1)
$^1$H-NMR: (CDCl$_3$) δ [ppm] 2.65 (OH, s 1H), 3.08 (OSO$_2$CH$_3$; s 3H), 3.57–4.40 (OCH$_2$, m about 135H)
One OH function/molecule still present (acetic anhydride/pyridine method)

(e) O-Mesyl-[P 41/300]

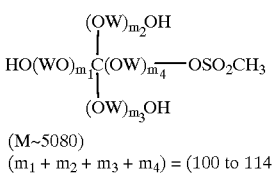

(M~5080)
(m$_1$ + m$_2$ + m$_3$ + m$_4$) = (100 to 114)

Feed: 0.01 mol of P 41/300, (molecular weight ~5000)
Purification: as in the general procedure for O-mesyl-polyalkylene glycol (1.)
Yield: 49.8 g (98%), viscous oil
TLC (RP 18), $R_F$=about 0.9 (CH$_3$OH:CH$_3$CN=7:3)
$^1$H-NMR: (CDCl$_3$) δ [ppm] 1.14 (CCH$_3$, m about 65H), 2.80 (OH, s 3H), 3.08 (OSO$_2$CH$_3$; s 3H), 3.20–4.40 (OCH$_2$, OCH, m about 420H)

The reaction product still contains 3 OH functions in random distribution (acetic anhydride/pyridine method)

General Procedure for the Synthesis of 4-(diphenylphosphinyl)phenoxy-polyalkylene Glycols and Ethers (Examples 7 to 16)

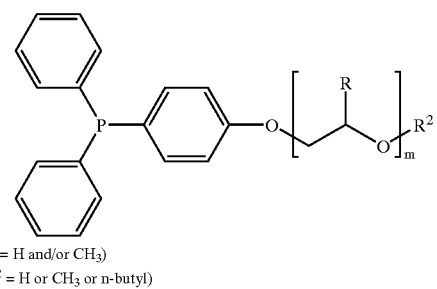

(R = H and/or CH$_3$)
(R$^2$ = H or CH$_3$ or n-butyl)

General procedure: The following reaction is carried out under nitrogen. 1.73 g (60 mmol) of NaH (80% strength) are initially introduced into 150 ml of DMF, and 16.7 g (60 mmol) of diphenyl-4-hydroxyphenylphosphine dissolved in 100 ml of DMF are carefully added dropwise at room temperature. When the evolution of gas has stopped, 50 mmol of O-mesyl-polyalkylene glycol dissolved in 50 ml of DMF are added, and the mixture is heated at 90–100° C. for from 8 to 10 hours.

For work-up, the DMF is evaporated off under reduced pressure, and the residue is taken up in 1000 ml of dichloromethane and washed with 3×250 ml of 0.2N sulfuric acid and with 2×250 ml of water. The organic phase is then dried over magnesium sulfate, and the solvent is evaporated off.

Purification of the reaction products: see Examples.

EXAMPLE 7

Preparation of 4-(diphenylphosphinyl)phenoxy-[M 350], Abbreviated to M350-TPP

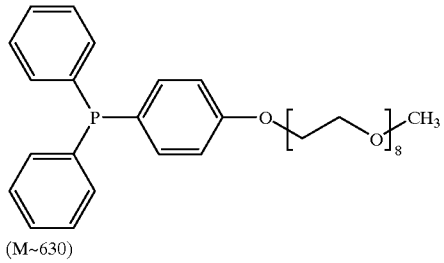

(M~630)

Feed: 0.05 mol of O-mesyl-[M 350], (molecular weight ~425)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH=$ 15:1

Yield: 23.6 g (75%), viscous oil

TLC, $R_F$=0.3 ($CH_2Cl_2:C_2H_5OH$=15:1)

$^1$H-NMR: ($CDCl_3$) δ [ppm] 3.38 ($OCH_3$, s 3H), 3.52–4.20 ($OCH_2$, m about 32H), 6.80–7.80 (arom. H, m about 14H)

$^{31}$P-NMR: 97% as phosphine and 3% as phosphine oxide

S<0.01%

EXAMPLE 8

Preparation of 4-(diphenylphosphinyl)phenoxy-[M 500], Abbreviated to (M 500-TPP)

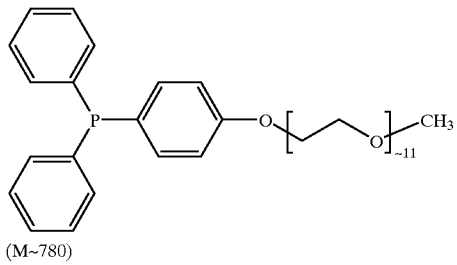

(M~780)

Feed: 0.05 mol of O-mesyl-[M 500], (molecular weight ~575)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH=$ 15:1

Yield: 32.3 g (83%), viscous oil

TLC, $R_F$=0.2 ($CH_2Cl_2:C_2H_5OH$=15:1)

$^1$H-NMR: ($CDCl_3$) δ [ppm] 3.38 ($OCH_3$, s 3H), 3.52–4.20 ($OCH_2$, m about 45H), 6.80–7.80 (arom. H, m about 14H)

$^{31}$P-NMR: 97% as phosphine and 3% as phosphine oxide

S 0.02%

EXAMPLE 9

Preparation of 4-(diphenylphosphinyl)phenoxy-[M 750], Abbreviated to (M750-TPP)

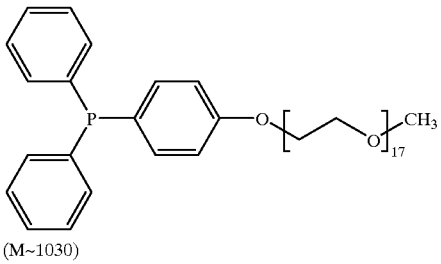

(M~1030)

Feed: 0.04 mol of O-mesyl-[M 750], (molecular weight ~825)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH=$ 15:1

Yield: 33.1 g (80%), viscous oil

TLC, $R_F$=0.27 ($CH_2Cl_2:C_2H_5OH$=15:1)

$^1$H-NMR: ($CDCl_3$) δ [ppm] 3.38 ($OCH_3$, s 3H), 3.52–4.20 ($OCH_2$, m about 69H), 6.80–7.80 (arom. H, m about 14H)

$^{31}$P-NMR: 97% as phosphine and 3% as phosphine oxide

S<0.01%

EXAMPLE 10

Preparation of 4-(diphenylphosphinyl)phenoxy-[M 41/40], Abbreviated to (M41/40-TPP)

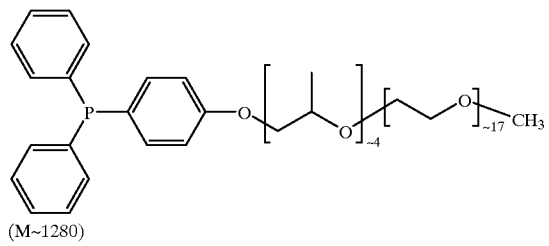

(M~1280)

Feed: 0.0212 mol of O-mesyl-[M 41/40], (molecular weight ~1075)

Purification: column chromatography [silica gel (φ 4.5 cm, h 30 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH$=9:1

Yield: 18.6 g (68.5%), viscous oil

TLC, $R_F$=0.21 ($CH_2Cl_2:C_2H_5OH$=9:1)

$^1$H-NMR: ($CDCl_3$) δ [ppm] 1.15 and 1.30 ($CCH_3$, 2d 12H), 3.38 ($OCH_3$, s 3H), 3.36–4.20 ($OCH_2$, m about 80H), 6.80–7.80 (arom. H, m about 14H)

$^{31}$P-NMR: 93% as phosphine and 7% as phosphine oxide

S 0.08%

EXAMPLE 11

Preparation of 4-(diphenylphosphinyl)phenoxy-[B 11/50], Abbreviated to (B 11/50-TPP)

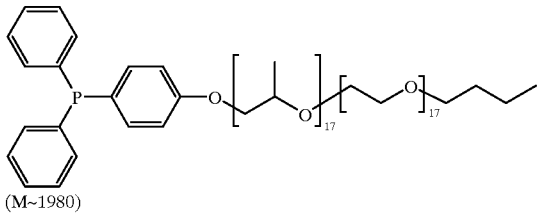

(M~1980)

Feed: 0.02 mol of O-mesyl-[B 11/50], (molecular weight ~1775)

Purification: column chromatography [silica gel (φ 4.5 cm, h 30 cm)] first the ethyl acetate to remove diphenyl-4-hydroxyphenylphosphine and its phosphine oxide, then ethyl acetate:$C_2H_5OH$=20:1

Yield: 13.8 g (35%), viscous oil $^1$H-NMR: ($CDCl_3$) δ [ppm] 0.92 (Bu $CH_3$, t 3H), 1.15 and 1.38 ($CCH_3$, $CCH_2C$, m 55H), 3.35–4.40 ($OCH_2$ and OCH, m about 121H), 6.80–7.80 (arom. H, m about 14H)

$^{31}$P-NMR: 82% as phosphine and 18% as phosphine oxide

S<0.01%

EXAMPLE 12

Preparation of 4-(diphenylphosphinyl)phenoxy-[PEG 200], Abbreviated to (PEG 200-TPP)

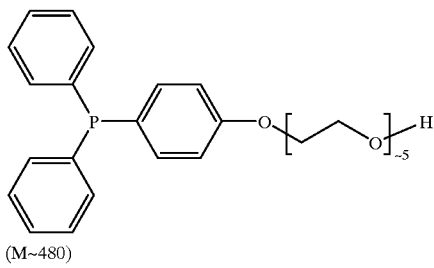

(M~480)

Feed: 0.054 mol of O-mesyl-[PEG 200], (molecular weight ~280)

Purification: column chromatography [silica gel (φ 4.5 cm, h 50 cm)] first the ethyl acetate to remove diphenyl-4-hydroxyphenylphosphine and its phosphine oxide, then ethyl acetate:$C_2H_5OH$=9:1

Yield: 19.0 g (75%), viscous oil

TLC, $R_F$=0.45 ($CH_2Cl_2$:$C_2H_5OH$=9:1)

$^1$H-NMR: ($CDCl_3$) δ [ppm] 2.80 (OH, br. s 1H), 3.52–4.20 ($OCH_2$, m about 20H), 6.86–7.70 (arom. H, m about 14H)

$^{31}$P-NMR: 96% as phosphine and 4% as phosphine oxide

S<0.01%

EXAMPLE 13

Preparation of 4-(diphenylphosphinyl)phenoxy-[PEG 600], Abbreviated to (PEG 600-TPP)

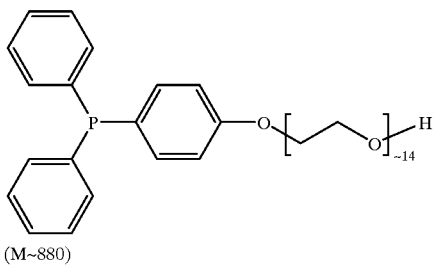

(M~880)

Feed: 0.022 mol of O-mesyl-[PEG 600], (molecular weight ~680)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2$:$C_2H_5OH$=18:1

Yield: 12.0 g (63%), viscous oil

TLC, $R_F$=0.35 ($CH_2Cl_2$:$C_2H_5OH$=9:1)

$^1$H-NMR: ($CDCl_3$) δ [ppm] 2.80 (OH, br. s 1H), 3.56–4.20 ($OCH_2$, m about 55H), 6.86–7.70 (arom. H, m about 14H)

$^{31}$P-NMR: 97% as phosphine and 3% as phosphine oxide

S<0.01%

EXAMPLE 14

Preparation of 4-(diphenylphosphinyl)phenoxy-[PEG 1000], Abbreviated to (PEG 1000-TPP)

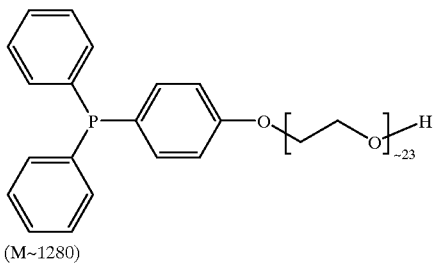

(M~1280)

Feed: 0.015 mol of O-mesyl-[PEG 1000], (molecular weight ~1080)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2$:$C_2H_5OH$=10:2

Yield: 9.2 g (50%), viscous oil

TLC, $R_F$=0.32 ($CH_2Cl_2$:$C_2H_5OH$=6:1)

$^1$H-NMR: ($CDCl_3$) δ [ppm] 2.80 (OH, br. s 1H), 3.56–4.20 ($OCH_2$, m about 75H), 6.86–7.70 (arom. H, m about 14H) (number of protons for PEG 1000 fraction too low since during chromatographic purification the low molecular weight fractions have been isolated in preference; using HPLC analysis, it is ensured that no 2 phosphine radicals are present per molecule in the product)

EXAMPLE 15

Preparation of 4-(diphenylphosphinyl)phenoxy-[PEG 1500], Abbreviated to (PEG 1500-TPP)

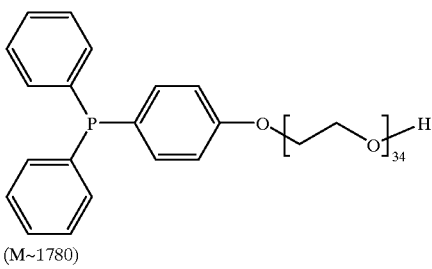

(M~1780)

Feed: 0.0126 mol of O-mesyl-[PEG 1500], (molecular weight ~1580)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH=9:1$ Yield: 10.2 g (46%), waxy product TLC, $R_f$=0.35 ($CH_2Cl_2:C_2H_5OH=6:1$)

$^1$H-NMR: ($CDCl_3$) δ [ppm] 2.80 (OH, br. s 1H), 3.56–4.20 ($OCH_2$, m about 136H), 6.86–7.70 (arom. H, m about 14H)

$^{31}$P-NMR: 93% as phosphine and 7% as phosphine oxide
S<0.01%

EXAMPLE 16

Preparation of 4-(diphenylphosphinyl)phenoxy-[P 41/300], Abbreviated to (P 41/300-TPP)

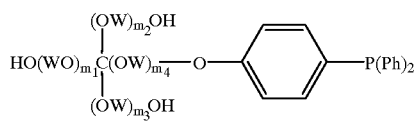

P41/300-TPP
(M~5260)
$m_1 + m_2 + m_3 + m_4$ = 100 to 114

Feed: 0.01 mol of O-mesyl-[P 41/300], (molecular weight ~5080)

Purification: column chromatography [silica gel (φ 4.5 cm, h 50 cm)] first the ethyl acetate to remove diphenyl-4-hydroxyphenylphosphine and its phosphine oxide, then $CH_2Cl_2$ to remove ethyl acetate, then $CH_2Cl_2:C_2H_5OH=10:1$ Yield: 10.2 g (46%), viscous oil TLC, $R_f$=0.56 ($CH_2Cl_2:C_2H_5OH=3:1$)

$^1$H-NMR: ($CDCl_3$) δ [ppm] 1.14 ($CCH_3$, m about 65H), 3.56–4.20 ($OCH_2$, m about 420H), 6.86–7.70 (arom. H, m about 14H)

$^{31}$P-NMR: 82% as phosphine and 18% as phosphine oxide
S<0.01%, P 0.52%

$^{31}$P-NMR: 96% as phosphine and 4% as phosphine oxide
S<0.01%

What is claimed is:

1. A compound of the formula (I)

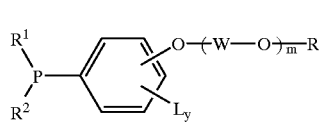

in which m is a number from 2 to 300;
y is a number from 0 to 4;
W is a group of the formulae $—CH_2—CH_2—$, $—CH(CH_3)CH_2—$ or $—CH_2CH(CH_3)—$;
R is hydrogen, a straight-chain or branched $C_1–C_5$-alkyl radical; or a group of the formulae

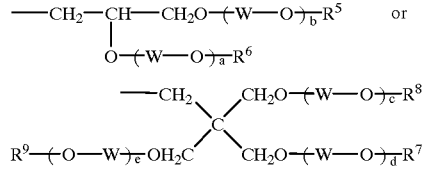

where
a, b, c, d and e independently of one another are numbered for 0 to 1000, at least one of the numbers a, b, c, d and e being greater than 0;
$R^5$, $R^6$, $R^7$, $R^8$ and $R^9$ are identical or different and are hydrogen $C_1–C_5$-alkyl or a group of the formula

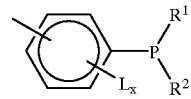

$R^1$ and $R^2$ are identical or different and are a straight-chain, branched or cyclic $C_1–C_{30}$-alkyl radical or $C_6–C_{10}$-aryl radical, which is unsubstituted or substituted by from one to five $C_1–C_3$-alkyl radicals, or $R^1$ and $R^2$, together with the trivalent P atom, form a dibenzophospholyl of the formula

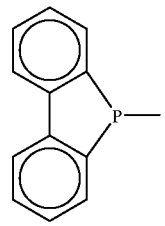

or a 3,4,-dimethylphospholyl of the formula

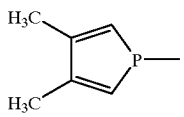

and
L is $C_1–C_5$-alkyl, $C_1–C_5$-alkoxy, $NO_2$, $NR^3R^4$, where $R^3$ and and $R^4$ independently of one another are hydrogen or $C_1–C_4$-alkyl, or L is Cl or OH, x is a number from 1 to 4, with proviso that when:
R$^1$ and R$^2$ are both phenyl;
Y is 0;
W is —CH$_2$—CH$_2$—;
R is hydrogen; and
the group —O—(W—O)$_m$—R is in the para-position relative to phosphorus
m is a number from 2 to 35; and the proviso that when:
R$^1$ and R$^2$ are both phenyl;
Y is 0;
W is —CH$_2$—CH$_2$—;
R is methyl; and
the group —O—(W—O)$_m$—R is in the para-position relative to phosphorus m is a number from 2 to 20.

2. A compound as claimed in claim 1, wherein R is hydrogen, methyl, ethyl, n-propyl, n-butyl or a group of the formula

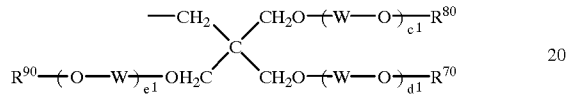

in which c$^1$, d$^1$ and e$^1$ independently of one another are a number from 1 to 500; and R$^{70}$, R$^{80}$ and R$^{90}$ are identical or different and are hydrogen, methyl, ethyl, n-propyl or n-butyl.

3. A compound as claimed in claim 1, wherein R$^1$ and R$^2$ are identical and are each a straight-chain or branched C$_1$–C$_6$-alkyl radical, a cyclohexyl radical or a phenyl radical.

4. A compound as claimed in claim 1, wherein L is methoxy, ethoxy, methyl, ethyl or OH.

5. A compound as claimed in claim 1, wherein y is 0.

6. A compound as claimed in claim 1, wherein m is a number from 2 to 100.

7. A compound as claimed in claim 2, in which c$^1$, d$^1$ and e$^1$ independently of one another are a number from 2 to 300.

8. A process for the preparation of a compound of the formula

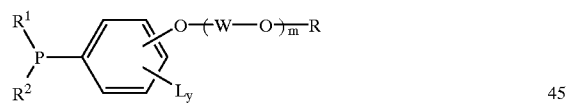

in which
m is a number from 2 to 300;
y is a number from 0 to 4;
W is a group of the formulae —CH$_2$—CH$_2$—, —CH(CH$_3$)CH$_2$— or —CH$_2$CH(CH$_3$)—;
R is hydrogen, a straight-chain or branched C$_1$–C$_5$-alkyl radical; or a group of the formulae

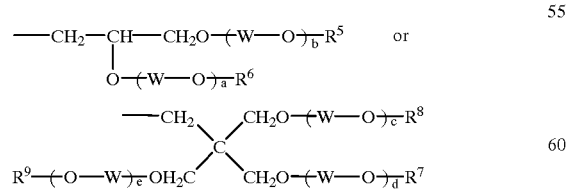

where
a, b, c, d and e independently of one another are numbered for 0 to 1000, at least one of the numbers a, b, c, d and e being greater than 0;

R$^5$, R$^6$, R$^7$, R$^8$ and R$^9$ are identical or different and are hydrogen, C$_1$–C$_5$-alkyl or a group of the formula R$^1$ and R$^2$ are identical or different and are a straight-chain, branched or cyclic C$_1$–C$_{30}$-alkyl radical or C$_6$–C$_{10}$-aryl radical, which is unsubstituted or substituted by from one to five C$_1$–C$_3$-alkyl radicals, or R$^1$ and R$^2$, together with the trivalent P atom, form a dibenzophospholyl of the formula or a 3,4,-dimethylphospholyl of the formula and
L is C$_1$–C$_5$-alkyl, C$_1$–C$_5$-alkoxy, NO$_2$, NR$^3$R$^4$, where R$^3$ and R$^4$ independently of one another are hydrogen or C$_1$–C$_4$-alkyl, or L is Cl or OH,
x is a number from 0 to 4, with proviso that when:
R$^1$ and R$^2$ are both phenyl;
Y is 0;
W is —CH$_2$—CH$_2$—;
R is hydrogen; and
the group —O—(W—O)$_m$—R is in the para-position relative to phosphorus
m is a number from 2 to 35; and the proviso that when:
R$^1$ and R$^2$ are both phenyl;
Y is 0;
W is —CH$_2$—CH$_2$—;
R is methyl; and
the group —O—(W—O)$_m$—R is in the para-position relative to phosphorus
m is a number from 2 to 20,
which comprises deprotonating a hydroxyphenylphosphine of the formula (II)

(II)

wherein R$^1$, R$^2$, L and y are defined above, with a base to give the corresponding phenoxide, and reacting it with a compound of the formula (III)

X—(—W—O—)$_m$—R    (III), in which W, R and m are defined above and X is a nucleophilic leaving group, to give a compound of the formula (I).

9. The process as claimed in claim 8, wherein X is an ortho-, meta- or para-toluenesulfonate, methanesulfonate, trifluoroacetate, trifluoromethanesulfonate, nonafluorobutylsulfonate, benzenesulfonate, p-nitrobenzenesulfonate, Cl, Br or I.

10. The process as claimed in claim 8, wherein the reaction is carried out in the presence or in the absence of an organic solvent.

11. A process as claimed in claim 8, wherein m is a number from 2 to 100.

* * * * *